United States Patent [19]

Hemmy et al.

[11] Patent Number: 5,098,383
[45] Date of Patent: Mar. 24, 1992

[54] DEVICE FOR ORIENTING APPLIANCES, PROSTHESES, AND INSTRUMENTATION IN MEDICAL PROCEDURES AND METHODS OF MAKING SAME

[75] Inventors: David C. Hemmy, Elm Grove, Wis.; Gregg S. Baker, Lake Forest; Paul B. Hafeli, El Toro, both of Calif.

[73] Assignee: Artifax Ltd., Newport Beach, Calif.

[21] Appl. No.: 476,951

[22] Filed: Feb. 8, 1990

[51] Int. Cl.⁵ .............................. A61M 5/00
[52] U.S. Cl. ........................... 604/116; 606/96
[58] Field of Search ................ 604/116; 606/96

[56] References Cited
U.S. PATENT DOCUMENTS

| 3,542,022 | 11/1970 | Bartnik | 604/116 |
|---|---|---|---|
| 3,941,127 | 3/1976 | Froning | 604/116 |
| 4,360,028 | 11/1982 | Barbier et al. | |
| 4,427,005 | 1/1984 | Tener | 604/116 |
| 4,436,684 | 3/1984 | White | |
| 4,497,325 | 2/1985 | Wedel | 604/116 |
| 4,580,561 | 4/1986 | Williamson | 604/116 |
| 4,638,799 | 1/1987 | Moore | 604/116 |
| 4,667,679 | 3/1987 | Sahota | 604/116 |
| 4,723,544 | 2/1988 | Moore et al. | 604/116 |
| 4,798,212 | 1/1989 | Arana | 604/116 |
| 4,827,918 | 5/1989 | Olerud | |
| 4,883,053 | 11/1989 | Simon | 604/116 |

Primary Examiner—Paul J. Hirsch
Attorney, Agent, or Firm—Finnegan, Henderson, Farabow, Garrett & Dunner

[57] ABSTRACT

A guide, and methods for its manufacture and use, for use with a medical instrument whereby the instrument must contact a patient's tissue at a particular location. Given the specific patient's tissue geometry, the general medical procedure and the specific practitioner's requests, if any, a nonadjustable guide is specifically manufactured such that one or more locations of the invention attaches to and/or abuts against a portion of patient tissue correctly orienting the device with respect to the patient's tissue geometry for purposes of performing the given medical task. The remaining geometric features of the device are dictated by the task for which it is designed and other characteristics of the tissue.

29 Claims, 4 Drawing Sheets

DEVICE FOR ORIENTING APPLIANCES, PROSTHESES, AND INSTRUMENTATION IN MEDICAL PROCEDURES AND METHODS OF MAKING SAME

BACKGROUND OF THE INVENTION

A. Field of the Invention

The present invention relates generally to devices used to establish proper orientation of medical instruments during medical procedures. The present invention also relates to methods for producing devices used for orienting instruments during medical procedures.

B. Description of the Prior Art

There are many medical procedures which are technically demanding on the physician. More particularly, certain medical procedures require, for example, the cutting, drilling, reaming, or shaping of tissue, specifically, bone. When a practitioner performs these tasks, a high degree of accuracy in establishing the proper orientation of medical instruments is required. In certain orthopedic and neurosurgical procedures these tasks can be extremely difficult because the practitioner must rely on locating a portion of the tissue, referred to as a landmark, and manually orient an instrument, appliance and/or prosthesis relative to that landmark.

While some instrumentation is available for fixing an apparatus to the tissue to aid the practitioner in orienting the instrument, appliance and/or prosthesis relative to the landmark, such existing devices must be manually adjusted via, for example, screws to properly orient the instrument, appliance or prosthesis before the medical task is performed. This manual adjustment may require the concurrent use of scanning X-ray equipment.

The inconvenience of requiring the practitioner, during a medical procedure, to manually adjust such a device, while monitoring other equipment, to properly orient the instrument, appliance or prosthesis is a disadvantage of the existing devices. Disadvantageously, such adjustment requires the additional time of the practitioner, of the operating facility in which the medical procedure is being performed and of the other personnel required to be present during the procedure to assist the practitioner, as well as a resulting additional expense to the patient. Most importantly, this disadvantage creates an added risk to the patient's life due to the additional time required to perform the procedure.

Another disadvantage is the great potential for inaccurate application of the instrument, appliance and/or prosthesis due to the adjustability of the existing devices. For example, using such a device, the practitioner may be required to make several failed attempts to properly orient an appliance or prosthesis before achieving the proper orientation for the appliance or prosthesis. Additionally, due to the adjustability of the conventional devices, there is a high probability that the practitioner may never achieve an accurate orientation of the appliance or prosthesis.

Still another disadvantage of the conventional devices is the additional cost in having the scanner X-ray equipment and a qualified operator available during the procedure.

SUMMARY OF THE INVENTION

The object of the present invention is to provide a simple and direct way by which a medical instrument may be precisely guided to a point of interest within the body. Stated otherwise, the object of the present invention is to provide the practitioner with the ability to establish orientation by use of a device which locates a point of interest, relative to a given landmark, and directly assists in performing the task at hand.

Another object of the present invention is to manufacture distinct patient and medical task specific devices, given information concerning the individual patient's tissue geometry at the given landmark location, the general medical procedure to be performed, the specific requests by the practitioner, if any, and the particular medical task at hand. The information concerning the individual patient's geometry can be supplied via one or more invasive or noninvasive modalities, e.g., exploratory surgery, radiograph, computed tomography scan, nuclear magnetic resonance, photon emission tomography, etc. This collection of data prior to fabricating the patient specific devices of the present invention makes possible the necessary precision required by a practitioner when preforming a medical procedure. The patient specific devices of the present invention, in conjunction with appropriate data, establishes a high probability of accuracy for the practitioner when applying the instrument, appliance and/or prosthesis for which the device was designed.

Still another advantage of the present invention is the reduced time required to perform the medical procedure, and resulting expense to the patient. Using the present invention, the practitioner merely has to locate the landmark surface and affix the device to the location. No further manual adjustment is required. The device then assists the practitioner in properly orienting the instrument, appliance and/or prosthesis and virtually eliminates any inaccurate application of the instrument, appliance and/or prosthesis.

Lastly, another object of the present invention is to minimize or to eliminate the need for scanning X-ray equipment and for a qualified operator of such equipment to be present during the medical procedure.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the device of the invention comprises a positioning means and an orienting means. The positioning means has a positioning surface, corresponding to a reference point on a surface of a landmark, determined prior to performing a medical task, for positioning the guide to remain in a fixed location with respect to the landmark surface.

The orienting means is fixedly connected to the positioning means and guides an instrument to be used in the medical task to contact a patient tissue at an appropriate location, determined prior to performing the medical task, when the guide is in the fixed location.

An embodiment of the present invention includes the positioning means, the orienting means and a securing means. The positioning means has a positioning surface, corresponding to a plurality of reference points on a surface of a landmark, determined prior to performing the medical task, for positioning the guide to remain in a fixed location with respect to the landmark surface. The positioning surface further comprises a portion wherein the portion matches a plurality of points on the landmark surface.

The orienting means is fixedly connected to the positioning means and guides an instrument to be used in the medical task to contact a patient tissue at an appropriate location, determined prior to performing the medical task, when the guide is in the fixed location. The orienting means further comprises an orienting portion defining a plurality of orienting holes, for guiding the instrument to contact the patient tissue at the appropriate location when the instrument is inserted in one of the orienting holes.

The securing means is connected to the positioning means, for removably attaching the device to the patient. The securing means includes a securing portion capable of attaching to, or being secured to, patient tissue, and optionally includes a hole through which a securing element may be inserted to contact patient tissue.

The present invention also is directed to a method of manufacturing a guide (e.g., a device according to the invention) out of a biocompatible material for performing a medical task during a medical procedure, wherein an instrument must contact a patient tissue at an appropriate location, and wherein a reference point, corresponding to a surface of a patient tissue to be used as a landmark, is determined prior to performing the medical task. The method is characterized by the steps of (a) collecting data regarding a patient tissue geometry including the reference point corresponding to the landmark surface, via a modality;

(b) collecting data concerning the medical procedure, the medical task to be performed and the instrument to be used during the task;

(c) fabricating the positioning means from the biocompatible material characterized by a positioning surface corresponding to the patient tissue geometry and to the data, for positioning the guide in a fixed location with respect to the landmark surface; and (d) fabricating the orienting means from the biocompatible material, fixedly connected to the positioning means and corresponding to the data, for guiding the instrument to contact the patient tissue at the appropriate location when the guide is placed in the fixed location.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

DESCRIPTION OF THE PREFERRED EMBODIMENT

Reference will now be made in detail to the present preferred embodiment of the invention, examples of which are illustrated in the accompanying drawings. Wherever possible, the same reference numbers will be used throughout the drawings to refer to the same or like parts.

Figure 1:
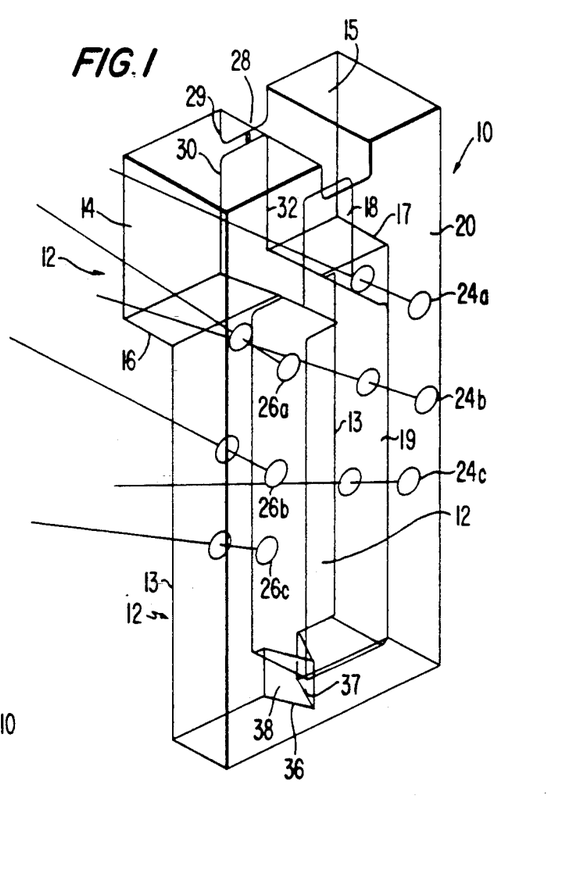
FIG. 1 is an isometric projection of an embodiment of the present invention.

The preferred embodiment of the present invention, as depicted in FIG. 1, is primarily designed for a procedure of drilling into bone. The present invention may also be used for other medical tasks, including but not limited to the cutting, reaming and shaping of tissue. In the preferred embodiment of the present invention, given a predetermined location of the body wherein a medical task is to be performed, a three-dimensional tissue geometry is constructed via a noninvasive method, e.g., radiograph, computed tomography scan, nuclear magnetic resonance or photon emission tomography. An invasive method, for example, exploratory surgery, also may be performed to gather the three-dimensional tissue geometry.

Given the specific patient's tissue geometry, the general medical procedure and the specific practitioner's requests, if any, the preferred embodiment of the present invention is specifically manufactured such that one or more locations of a device according to the invention attaches to and/or abuts against a specific surface in order to correctly orient the device with respect to the patient's tissue geometry for purposes of performing the given medical task. The remaining geometric features of the device are dictated by the task for which it is designed and other characteristics of the tissue. For example, the preferred embodiment of the present invention may contain one or more holes used by a practitioner for establishing the location of drill holes in the bone for the purpose of performing certain medical tasks with conventional medical instruments. The device according to the present invention also may contain one or more openings, surfaces, contours, templates or indicators used by the practitioner for establishing the location of cut planes, drill holes, shaping surfaces or reference vectors for the purpose of performing a variety of medical tasks with a variety of medical instruments, e.g., emplacement of a supporting plate.

Figure 2:
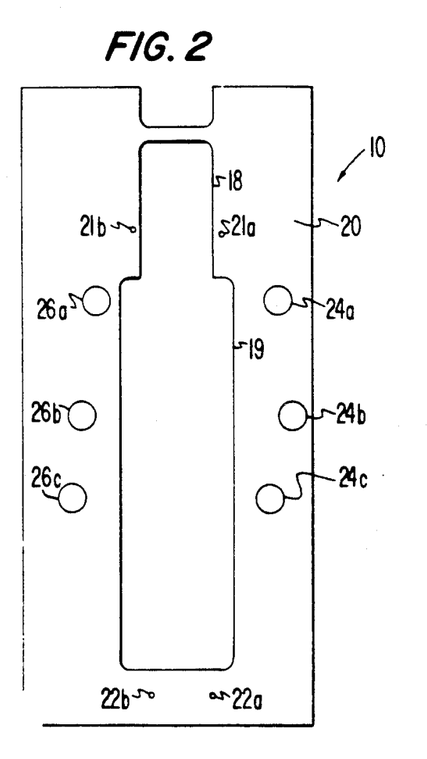
FIG. 2 is a top view of the embodiment.
Figure 3:
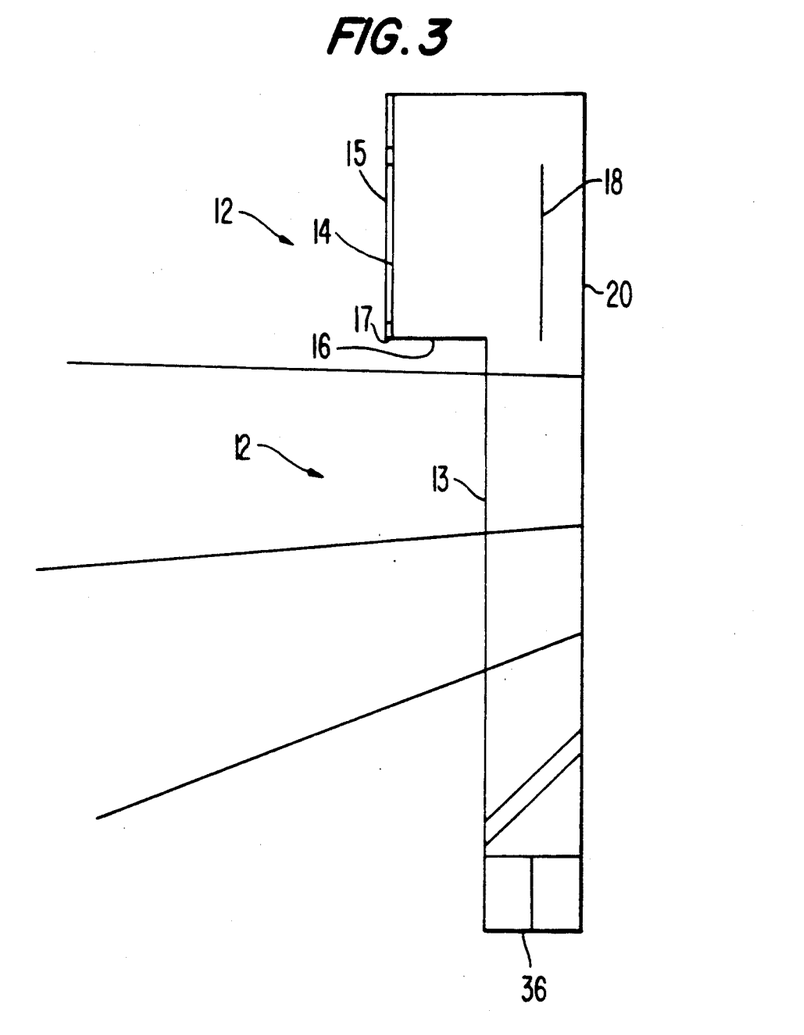
FIG. 3 is a side view of the embodiment.

Referring to the accompanying figures, FIGS. 1-3, it may be seen that the preferred embodiment of the present invention provides a guide 10, for performing a medical task during a medical procedure, wherein an instrument must contact a patient tissue at appropriate locations, and wherein a plurality of reference points, corresponding to surfaces to be used as landmarks, are determined prior to performing the medical task. A landmark may be, for example, a unique surface of a patient tissue and/or an installed synthetic surface. This embodiment was designed to properly orient screw hole locations and depth for insertion of screws into the bony tissue surrounding the spine for securing a plate (not shown) to three vertebras of the spinal column using unique surfaces of a patient tissue as landmarks.

In addition to the guide 10 of the present embodiment, the medical instruments required to perform this task are, for example, screws, cross pins, guide sleeves, a drill with stop, a tap, a screwdriver and a nut driver.

The plurality of reference points, corresponding to surfaces of a patient tissue to be used as landmarks, are determined by means of a method for determining a three dimensional patient tissue geometry as described, for example, in 5 Radiology of the Skull and Brain, Technical Aspects of Computed Tomography (1980). The body is subjected to radiant energy to produce radiant energy responses internal to the body. The radiant energy responses are detected to obtain representations of substances at locations internal to the body. Finally, a set of three dimensional coordinates is generated and defines a three dimensional representation of one or more selected landmarks, which in this particularly case are internal to the body.

Once the three dimensional patient tissue geometry of the landmark surfaces is generated, the preferred embodiment of the present invention may be manufactured. Prior to fabricating the device of the preferred embodiment, using the specific patient tissue geometry, other data concerning the procedure to be performed, for example, the placement of screw hole locations on the patient tissue, as well as the angle and depth of the screw holes is determined. Finally, after this information concerning the procedure and any additional information from the practitioner is obtained, the guide 10 can be fabricated from biocompatible material.

In accordance with the preferred embodiment, the present invention comprises a positioning means, an orienting means and a securing means. The orienting means and the securing means are fixedly connected to the positioning means in, for example, a unitary body or monolithic structure.

Figure 4:
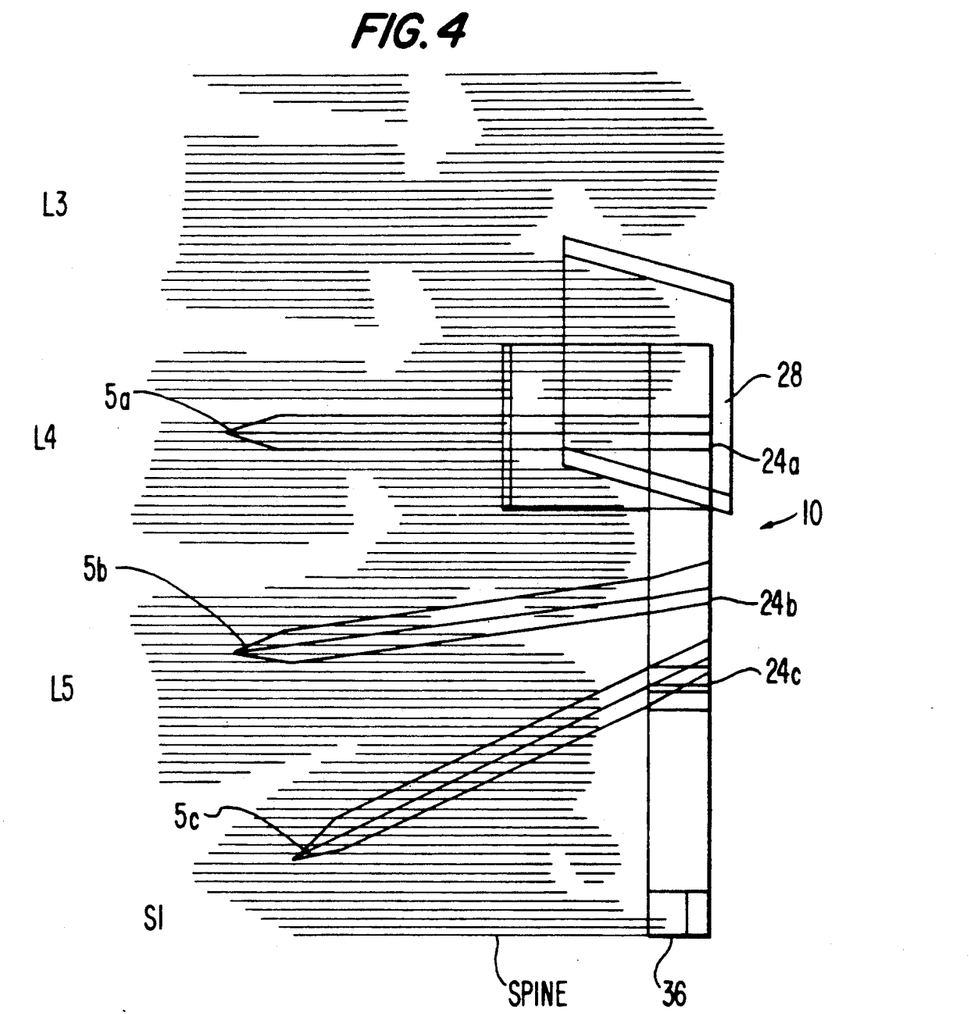
FIG. 4 is a side view of the embodiment placed adjacent to a spine.

As illustrated in FIG. 4, the proximal end of the guide 10 is determined by the location of the guide 10 with respect to the location of the head. That side of the guide 10, closest to the head, when the guide 10 is placed on the spinal column, is referred to as the proximal end.

In accordance with the preferred embodiment, the guide 10 as illustratively shown is FIGS. 1 and 2, comprises a posterior surface 20. Also depicted in FIGS. 1 and 2 is the guide 10 which defines numerous hollow openings from the posterior surface 20, through the guide 10, to a positioning surface 12. In FIG. 1 these openings include a proximal hollow portion 18, a viewing hollow portion 19 and a plurality of orienting holes 24 a-c on the right side of the guide 10 and a plurality of orienting holes 26 a-c on the left side of the guide 10. All of these openings are fabricated in the guide 10 in accordance with instructions concerning the medical task to be performed and the specific patient tissue geometry adjacent to where the task is going to be performed. Most important to the present embodiment, the proximal hollow portion 18, defined by the guide 10, permits the practitioner to confirm proper placement of the positioning surface 12 on a landmark surface. The viewing hollow portion 19 allows the practitioner to view a patient tissue adjacent to landmark surfaces.

In accordance with this embodiment of the present invention, the positioning means is characterized by having the positioning surface 12. As illustratively shown in FIGS. 1 and 3, by way of example and not limitation, the positioning surface 12 is provided, a portion of which corresponds to the plurality of reference points of the patient tissue geometry, for positioning the guide 10 to remain in a fixed location with respect to the landmark surfaces. The positioning surface 12 includes a surface portion 13 and two positioning portions 28 and 36. The positioning portions respectively correspond to subgroups of the plurality of reference points on the surface of a patient tissue previously referred to as surface landmarks.

The proximal positioning portion 28 is located at the proximal end on the guide 10. The distal positioning portion 36, located at the distal end of the guide 10, substantially axially spaced from the proximal positioning portion 28, corresponds to a subgroup of the plurality of reference points which form, for example, a contour surface which matches or compliments a landmark surface.

The proximal positioning portion 28 of the positioning surface 12, as depicted in FIG. 1, by way of example and not limitation, comprises the proximal positioning surfaces 14 and 15. The proximal positioning surfaces 14 and 15, varying in depth from the surface portion 13 by proximal offset positioning portions 16 and 17 respectively, contain sufficient geometric features to constitute a surface or contour which matches and/or complements a landmark surface, or at least to constitute a surface that mates to or engages the landmark. The varying depth of each of the offset proximal positioning portions 16 and 17 is determined by the three dimensional patient tissue geometry. This enables the positioning surface 12, including the proximal positioning surfaces 14 and 15, to lie adjacent to and/or abut against landmark surfaces.

As stated earlier, the proximal hollow portion 18, defined by inside surfaces 29, 31, and 32 of the guide 10, illustrated in FIG. 1, permits the practitioner to establish proper placement of the positioning surface 12 of the guide 10, including the proximal positioning portion 28, on the spinal column adjacent to the location on the spinal column where the medical task is to be performed. The inside surfaces 29, 31 and 32 of the proximal hollow portion 18 contact a surface of a landmark.

The distal positioning portion 36 of the positioning surface 12 is V-shaped and comprises a two-sided surface including a right-side distal positioning surface 37 and a left-side distal positioning surface 38. The V-shaped distal positioning portion 36 comprised of the right-side distal positioning surface 37 and the left-side distal positioning surface 38, also contain sufficient geometric features to constitute a surface or contour which matches and/or complements another landmark surface, or a surface which engages the landmark surface.

As stated earlier, the viewing hollow portion 19 of the guide 10 allows the practitioner to view a patient tissue adjacent to the landmark surfaces corresponding to the positioning portions 28 and 36 of the positioning surface 12 of the guide 10. Further variation of the present invention would be apparent to one skilled in the art by adding multiple positioning surfaces and/or multiple contours to the present embodiment.

In accordance with the present embodiment, as depicted in FIGS. 1 and 2, the orienting means, fixedly connected to the positioning means, is characterized by having an orienting portion defining a plurality of orienting holes, 24 a-c and 26 a-c, for guiding instruments inserted in the orienting holes 24 a-c and 26 a-c to contact the patient tissue at the appropriate locations when the guide is in the fixed location. In addition to the orienting holes 24 a-c and 26 a-c, FIG. 1 depicts the reference vector lines corresponding to each of the orienting holes 24 a-c and 26 a-c. These vectors indicate the predetermined angles the orienting holes 24 a-c and 26 a-c manufactured in the guide 10. In this embodiment the orienting holes 24 a-c and 26 a-c guide a drill bit to contact the patient tissue at the appropriate locations, indicated by the reference vectors, adjacent to the positioning surface 12, and to drill a hole into the patient tissue at the correct angle and depth. Additionally, the orienting holes 24 a-c and 26 a-c guide other instruments to perform other tasks during the medical procedure, e.g., guiding screws to the appropriate tissue locations.

Figure 5:
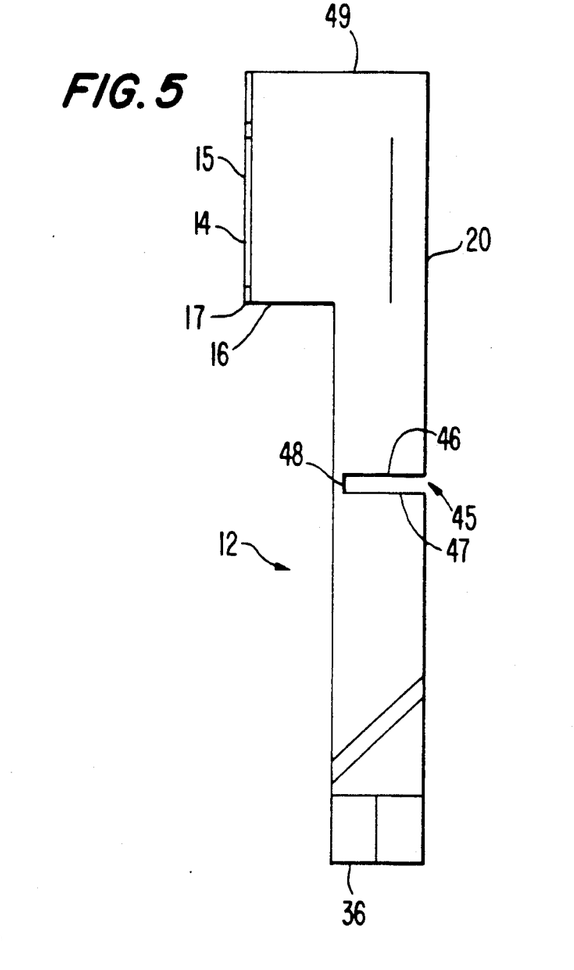
FIG. 5 is a side view of the embodiment with an orienting surface.

It will be apparent to those skilled in the art that various modifications and variations can be made in the orienting portion of the present invention and in construction of the orienting portion without departing from the scope or spirit of the invention. As an example, as illustratively shown in FIG. 5, the orienting portion may include an orienting slit 45 to guide a saw to contact an appropriate patient tissue location. The orienting slit 45 may contain a proximal orienting slit surface 46, a distal orienting slit surface 47 and a lower orienting slit surface 48 which form a miter box-type groove in the upper surface 20 of the guide 10 to guide a saw inserted in the groove to contact a patient tissue at the appropriate location. In a second example, the orienting portion may include an orienting surface 49 to guide a saw, placed adjacent to the orienting surface 49, to contact a patient tissue at the appropriate location. In still another example, the orienting portion may define an orienting template with proximal and distal template surfaces, to guide an instrument to contact a patient tissue at the appropriate location. It would be apparent to one skilled in the art that the orienting portion may include any combination of orienting holes and/or orienting surfaces.

Figure 6:
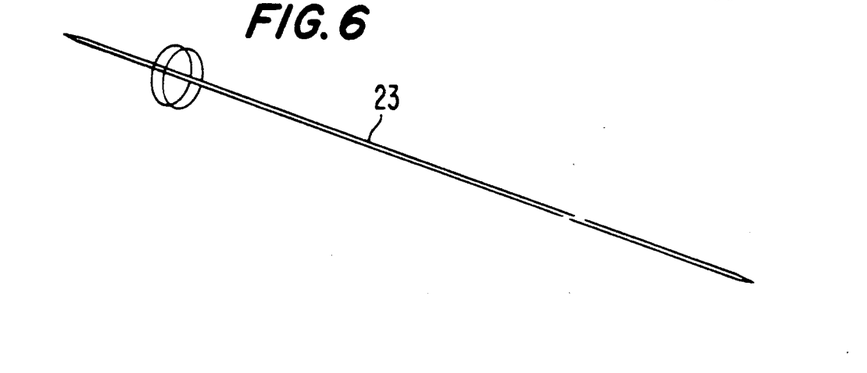
FIG. 6 is a cross pin with stop to be inserted through a single positioning hole depicted in FIG. 2.

In accordance with the present invention, the securing means, fixedly connected to the positioning means, is for removable attachment of the positioning surface adjacent to the patient tissue used as landmarks. As an example, the present embodiment characterizes the securing means as including a securing portion which defines a plurality of securing holes. As illustratively shown in FIG. 2, by way of example and not limitation, securing holes 21 a-b and 22 a-b are located at opposite ends of the guide, two at the proximal end 21 a-b and two at the distal end 22 a-b, above the respective positioning portions 28 and 36. Securing devices, for example, a cross pin with a stop 23 depicted in FIG. 6, may be inserted through the securing holes 21 a-b and 22 a-b at a predetermined angle to contact the patient tissue adjacent to the landmarks and to secure the guide 10 to the patient tissue. It will be apparent to those skilled in the art that various modifications and variations can be made in the securing means of the present invention and in construction of the securing means portion without departing from the scope or spirit of the invention.

Now an example of a medical procedure using the preferred embodiment of the present invention will be described. As discussed earlier, prior to performing the procedure, the patient's three dimensional tissue geometry, corresponding to the location along the spinal column where a standard metal plate is to be secured to fuse two or more vertebras together, is determined via a noninvasive means, e.g., a standard CT scan. Many components of the present invention are designed for the individual patient's tissue geometry.

The metal plate described above is secured with screws. The placement of the screws, screw hole orientation and depth, is provided at each screw location with the custom instrumentation of the present invention. Additionally, each screw is manufactured to a prescribed length and the plates are manufactured to match the final screw placement in the spinal column.

Generally, the instrumentation required to perform the procedure includes:
1) The guide of the preferred embodiment of the present invention manufactured from biocompatible, autoclaveable plastic which functions to orient the screw holes to specific bony tissue landmarks.
2) Cross Pins: For example, stainless steel pins with depth stops to secure the guide at proximal and distal locations.
3) Guide sleeves: Cylindrical plastic sleeves to be installed in the guide to establish screw hole orientation and depth.
4) Drill with Stop: Conventional surgical drill with chuck and pin cutter, to drill the screw holes to a prescribed orientation and depth.
5) Tap: Standard instrumentation used to thread a screw hole with 5 mm incremental markings.
6) Screwdriver: Standard instrumentation with 5 mm incremental markings.
7) Nut driver: Standard instrumentation.

To begin the procedure, the practitioner clears the soft tissue from the landmark locations. The practitioner then determines the spinous process, referred to as the proximal landmark, adjacent to which the proximal positioning portion 28 and the proximal hollow portion 18 of the guide 10 are to be fixed. The next step would be to place the drill guide proximal contour positioning portion 28 over the preselected spinous process. The practitioner would then press firmly on the posterior surface 20 of the guide 10 over the spine to ensure that the guide 10 rests properly at both the proximal landmark, adjacent the proximal contour positioning portion 28, and at a distal landmark, adjacent the distal contour positioning portion 36, substantially axially spaced from the proximal landmark along the spine. If the guide 10 appears unstable, then the practitioner would remove the guide 10, remove any impediments, e.g., soft tissue interfering with placement of the guide 10, and replace the guide 10 to its proper position. Confirming proper placement of the guide 10 using the proximal hollow portion 18 and holding the guide 10 stable on the spine, the next step is to insert the proximal and distal cross pins in the positioning holes 21 a-b and 22 a-b to contact the patient tissue and to secure the guide 10.

Now that the guide is secured in place, the practitioner would proceed by placing the guide sleeves in the orienting holes 24 a-c and 26 a-c matching each sleeve to its correct location. Using the viewing hollow portion 19 to view the patient tissue during the task, the practitioner would then proceed, using a proper drill bit to accommodate a standard 2 mm Steinman pin, by inserting the bit successively into each guide sleeve and drilling a ⅓ of the full depth hole into the bone adjacent to the orienting holes 24 a-c and 26 a-c. Standard 2 mm Steinman pins are then inserted through each of the guide sleeves into the holes in the bony tissue. To ensure that the final placement of the screws and plates will be accurate the practitioner may then confirm proper orientation of the screw holes in the bony tissue radiographically.

Once confirming the orientation of the holes, the practitioner would then redrill the holes to full depth. Once all of the holes are completed, the guide sleeves are removed from the orientation holes 24 a-c and 26 a-c of the guide 10. The standard tap is then successively placed through each of the orientation holes 24 a-c and 26 a-c to thread the screw holes to the prescribed depth. The conventional screws 5 a-c, depicted in FIG. 4, which are specially manufactured to the prescribed length are then successively inserted through the orientation holes 24 a-c and installed to the prescribed depth. The same procedure would then be performed to install similar screws using orientation hole 26 a-c. The guide 10 is then detached from the spinal column by removing the cross pins.

Followed by the installation of a spacer, a lower nut is secured to each of the screws. The practitioner would then install the custom metal plates onto the lower nuts noting the left and right locations. Finally to complete the task, the practitioner would secure the plates with an upper nut on each of the screws implanted in the bony tissue of the spinal column.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Obviously, numerous modifications and variations of the present invention are possible in light of the above teachings. It is therefore to be understood that within the scope of the appended claims, the invention may be practised otherwise than as specifically described by the herein.

What is claimed is:

1. A guide for performing a medical task during a medical procedure, wherein an instrument must contact a patient tissue at an appropriate location, and wherein a reference point corresponding to a three-dimensional tissue geometry of the patient tissue, and corresponding to a surface of a landmark, is determined prior to performing the medical task, the guide comprising:
   positioning means, having a predefined positioning surface, for positioning the guide to remain in a fixed location with respect to the landmark surface, wherein the positioning surface has a three-dimensional configuration corresponding to the reference point; and
   orienting means, fixedly connected to the positioning means, for guiding the instrument to contact the patient tissue at the appropriate location when the guide is in the fixed location.

2. The guide of claim 1 wherein the positioning surface is placed adjacent to the landmark surface during the medical task.

3. The guide of claim 1 wherein the positioning surface further comprises a portion wherein the portion matches a plurality of points of the landmark surface.

4. The guide of claim 2 wherein the positioning surface further comprises a portion wherein the portion matches a plurality of points of the landmark surface.

5. The guide of any of claims 1-14 4 wherein the orienting means further comprising an orienting portion defining an orienting hole, for guiding the instrument to contact the patient tissue at the appropriate location when the instrument is inserted in the orienting hole.

6. The guide of any of claims 1-4 wherein the orienting means further comprises an orienting portion defining an orienting surface, for guiding the instrument to contact the patient tissue at the appropriate location when the instrument is placed adjacent to the orienting surface.

7. The guide of claim 1 further comprises securing means, connected to the positioning means, for attaching the positioning surface to the landmark surface.

8. The guide of claim 7 wherein the securing means includes a securing portion defining a securing hole.

9. The guide of claim 1 further comprises securing means, connected to the positioning means, for removably attaching the positioning surface to the landmark surface 10. The guide of claim 9 wherein the securing means includes a securing portion defining a securing hole.

11. A guide for use with an instrument in performing a medical task during a medical procedure on a patient tissue, wherein the instrument must contact a patient tissue at an appropriate location, and wherein a reference point corresponding to a three-dimensional tissue geometry of the patient tissue, and corresponding to a surface of a patient tissue used as a landmark, is determined prior to performing the task, and wherein the guide is a monolithic structure, the monolithic structure comprising:
   positioning means for positioning the guide to fit along the landmark surface, wherein the positioning means has a predefined positioning surface, and the positioning surface is placed adjacent to the landmark surface during the task, wherein the positioning surface has a three-dimensional configuration corresponding to the reference point; and
   orienting means, fixedly connected to the positioning means, for guiding the instrument to contact the patient tissue at the appropriate location when the positioning surface is placed adjacent to the landmark surface.

12. The monolithic structure of claim 11 wherein the orienting means further comprises an orienting portion defining an orienting opening, for guiding the instrument to contact the patient tissue at the appropriate location when the instrument is placed adjacent to the orienting opening.

13. The monolithic structure of claim 11 wherein the orienting means further comprises an orienting portion defining an orienting surface, for guiding the instrument to contact the patient tissue at the appropriate location when the instrument is placed adjacent to the orienting surface.

14. The monolithic structure of claim 11 wherein the instrument must contact a patient tissue at a plurality of appropriate locations, and wherein the orienting means further comprises an orienting portion defining a plurality of orienting openings, for guiding the instrument to contact the patient tissue at the appropriate locations when the instrument is placed adjacent to the plurality of orienting openings.

15. The monolithic structure of claim 11 further comprising securing means, connected to the positioning means, for attaching the positioning surface adjacent to the landmark surface.

16. The monolithic structure of claim 15 wherein the securing means includes a securing portion defining a plurality of securing holes, for guiding a securing device to contact the patient tissues when the securing device is inserted in the securing hole.

17. The monolithic structure of claim 11 further comprising securing means, connected to the positioning means, for removably attaching the positioning surface to the landmark surface.

18. The monolithic structure of claim 17 wherein the securing means includes a securing portion defining a securing hole, for guiding a securing device to contact the patient tissue when the securing device is inserted in the securing hole.

19. The monolithic structure of claim 11 wherein a plurality of reference points, corresponding to the surface of the patient tissue used as a landmark, are determined prior to performing the task, and wherein the positioning means has the positioning surface which corresponds to the plurality of reference points.

20. The monolithic structure of claim 19 wherein the positioning surface provides a contour which matches a contour of the landmark surface.

21. The monolithic structure of claim 19 wherein the positioning surface corresponds to the plurality of reference points and wherein the positioning surface provides a contour which matches a contour of the landmark surface.

22. A guide, for performing a medical task during a medical procedure wherein an instrument must contact a patient tissue at an appropriate location, and wherein a reference point corresponding to a three-dimensional tissue geometry of the patient tissue, and corresponding to a subgroup of a plurality of reference points on a surface of a patient tissue to be used as a landmark, is determined prior to performing the medical task, the guide comprising:

positioning means, having a predefined positioning surface, for positioning the guide to fit along the landmark, and the positioning surface is placed adjacent to the landmark during the task, wherein the positioning surface has a three-dimensional configuration corresponding to the subgroup of the plurality of reference points; and orienting means, fixedly connected to the positioning means, for guiding the instrument to contact the patient tissue at the appropriate location when the positioning surface is placed adjacent to the landmark.

23. The guide of claim 22 wherein the positioning surface further comprises a contour portion, corresponding to a subgroup of the plurality of reference points, which matches the contour of a landmark.

24. The guide of claim 22 wherein the orienting means further comprises an orienting portion defining an orienting hole, wherein the instrument is inserted in the orienting hole and guided to contact the patient tissue at the appropriate location when the guide is in the fixed location.

25. The guide of any of claims 22-23 wherein the orienting means further comprises an orienting surface, for guiding the instrument to contact the patient tissue at the appropriate location when the instrument is placed adjacent to the orienting surface.

26. The guide of claim 22 further comprising a securing means, fixedly connected to the positioning means, for removable attachment of the positioning surface adjacent to the landmark.

27. The guide of claim 26 wherein the securing means includes a securing portion defining a plurality of securing holes.

28. The guide of claim 23 further comprising a securing means, fixedly connected to the positioning means, for removable attachment of the positioning surface adjacent to the landmark.

29. The guide of claim 28 wherein the securing means includes a securing portion defining a securing hole.

* * * * *

UNITED STATES PATENT AND TRADEMARK OFFICE
CERTIFICATE OF CORRECTION

PATENT NO. : 5,098,383

DATED : March 24, 1992

INVENTOR(S) : David C. Hemmy et al.

It is certified that error appears in the above-identified patent and that said Letters Patent is hereby corrected as shown below:

On title page, item [73]
Assignee: change "Artifax Ltd." to --Artifex Ltd.--.

Signed and Sealed this

Fourteenth Day of September, 1993

Attest:

BRUCE LEHMAN

Attesting Officer   Commissioner of Patents and Trademarks